(12) United States Patent
Pinsky

(10) Patent No.: US 10,631,792 B2
(45) Date of Patent: Apr. 28, 2020

(54) SYSTEM AND METHOD OF DETERMINING A SUSCEPTIBILITY TO CARDIORESPIRATORY INSUFFICIENCY

(71) Applicant: University of Pittsburgh—of the Commonwealth System of Higher Education, Pittsburgh, PA (US)

(72) Inventor: Michael R. Pinsky, Pittsburgh, PA (US)

(73) Assignee: UNIVERSITY OF PITTSBURGH—OF THE COMMONWEALTH SYSTEM OF HGIHER EDUCATION, Pittsburgh, PA (US)

(*) Notice: Subject to any disclaimer, the term of this patent is extended or adjusted under 35 U.S.C. 154(b) by 1147 days.

(21) Appl. No.: 14/137,576

(22) Filed: Dec. 20, 2013

(65) Prior Publication Data

US 2014/0107437 A1 Apr. 17, 2014

Related U.S. Application Data

(63) Continuation of application No. PCT/US2012/045068, filed on Jun. 29, 2012.
(Continued)

(51) Int. Cl.
*A61B 5/00* (2006.01)
*A61B 5/021* (2006.01)
(Continued)

(52) U.S. Cl.
CPC .......... *A61B 5/7275* (2013.01); *A61B 5/0022* (2013.01); *A61B 5/01* (2013.01);
(Continued)

(58) Field of Classification Search
CPC ..... A61B 5/7275; A61B 5/01; A61B 5/02028; A61B 5/02055; A61B 5/02108;
(Continued)

(56) References Cited

U.S. PATENT DOCUMENTS

| 6,370,424 B1 | 4/2002 | Prutchi |
| 7,077,810 B2 | 7/2006 | Lange et al. |

(Continued)

FOREIGN PATENT DOCUMENTS

| JP | 2007-190080 | 8/2007 |
| JP | 2011-110063 | 6/2011 |

(Continued)

OTHER PUBLICATIONS

Defining the Incidence of Cardio respiratory Instability in Patients in Step-down Units Using an Electronic Integrated Monitoring System. by: Hrvnak et al. (Year: 2008).*
(Continued)

*Primary Examiner* — Gary Jackson
*Assistant Examiner* — Zahed Kabir
(74) *Attorney, Agent, or Firm* — Baker Botts L.L.P.

(57) ABSTRACT

A system and method for determining a patient's susceptibility to develop cardiorespiratory instability wherein physiological parameters are analyzed with respect to a dynamics systems model to produce and indicator associated with a probability that the patient will become unstable is provided.

42 Claims, 9 Drawing Sheets

Related U.S. Application Data

(60) Provisional application No. 61/503,344, filed on Jun. 30, 2011.

(51) Int. Cl.

| | |
|---|---|
| *A61B 5/01* | (2006.01) |
| *A61B 5/02* | (2006.01) |
| *A61B 5/1455* | (2006.01) |
| *A61B 5/145* | (2006.01) |
| *A61B 5/0205* | (2006.01) |
| *A61B 5/029* | (2006.01) |
| *G16H 50/20* | (2018.01) |
| *G16H 50/70* | (2018.01) |
| *A61B 5/024* | (2006.01) |

(52) U.S. Cl.
CPC .......... *A61B 5/029* (2013.01); *A61B 5/02028* (2013.01); *A61B 5/02055* (2013.01); *A61B 5/02108* (2013.01); *A61B 5/14539* (2013.01); *A61B 5/14551* (2013.01); *A61B 5/742* (2013.01); *A61B 5/7475* (2013.01); *G16H 50/20* (2018.01); *G16H 50/70* (2018.01); *A61B 5/02405* (2013.01)

(58) Field of Classification Search
CPC . A61B 5/029; A61B 5/14539; A61B 5/14551; A61B 5/742; A61B 5/7475; A61B 5/02405; G06F 19/3443; G06F 19/345; G16H 50/70
USPC ......................................................... 600/301
See application file for complete search history.

(56) References Cited

U.S. PATENT DOCUMENTS

| | | | | |
|---|---|---|---|---|
| 7,801,591 | B1* | 9/2010 | Shusterman | A61B 5/0205 600/509 |
| 7,938,782 | B2 | 5/2011 | Stahmann et al. | |
| 2004/0215090 | A1* | 10/2004 | Erkkila | A61B 5/02405 600/515 |
| 2005/0004608 | A1* | 1/2005 | Bullinga | A61N 1/3702 607/9 |
| 2006/0271407 | A1* | 11/2006 | Rosenfeld | A61B 5/412 705/3 |
| 2007/0073181 | A1* | 3/2007 | Pu | A61B 5/0816 600/529 |
| 2007/0088222 | A1* | 4/2007 | Berkow | A61B 5/02416 600/485 |
| 2007/0293779 | A1* | 12/2007 | Bardy | A61B 5/0031 600/529 |
| 2008/0125666 | A1* | 5/2008 | Crozier | A61B 5/044 600/509 |
| 2008/0214904 | A1* | 9/2008 | Saeed | A61B 5/0006 600/301 |
| 2008/0221468 | A1* | 9/2008 | Stahmann | A61B 5/0031 600/529 |
| 2008/0275349 | A1* | 11/2008 | Halperin | A61B 5/0205 600/484 |
| 2009/0006061 | A1* | 1/2009 | Thukral | G06F 19/325 703/11 |
| 2009/0048497 | A1* | 2/2009 | Keren | A61B 5/02028 600/301 |
| 2009/0143655 | A1* | 6/2009 | Shani | A61B 5/0059 600/323 |
| 2009/0275848 | A1* | 11/2009 | Brockway | A61B 5/0205 600/513 |
| 2010/0057490 | A1* | 3/2010 | Kocis | G06Q 50/22 705/2 |
| 2010/0179438 | A1 | 7/2010 | Heneghan et al. | |
| 2010/0256463 | A1 | 10/2010 | Greenwald et al. | |
| 2010/0278405 | A1* | 11/2010 | Kakadiaris | G16H 50/30 382/131 |
| 2010/0332249 | A1* | 12/2010 | Chbat | G06Q 50/22 705/2 |
| 2011/0144967 | A1* | 6/2011 | Adirovich | G16H 40/63 703/11 |

FOREIGN PATENT DOCUMENTS

| | | |
|---|---|---|
| WO | WO 2007/142968 A2 | 12/2007 |
| WO | WO 2010/14497 | 2/2010 |
| WO | WO 2010/77305 | 7/2010 |

OTHER PUBLICATIONS

English translation of JP Office Action dated May 12, 2015 in JP Patent Application No. 2014-519183.
International Search Report for PCT/US2012/045068, dated Dec. 26, 2012.
Extended European Search Report dated Nov. 19, 2018 in Application No. EP 18170946.

* cited by examiner

Derived 5 minute intra-epoch features from HR, RR and SpO2

| Time Domain | Frequency Domain | Entropy |
|---|---|---|
| Mean(EM) | Low frequency power(LO) | Approximate entropy (Ap) |
| Median | High frequency power(HI) | Sample entropy (Se) |
| Standard deviation(ESD) | LO/HI ratio | |
| Auto correlation | Total power (TP) | |
| Cross-correlation(X,XT) | | |

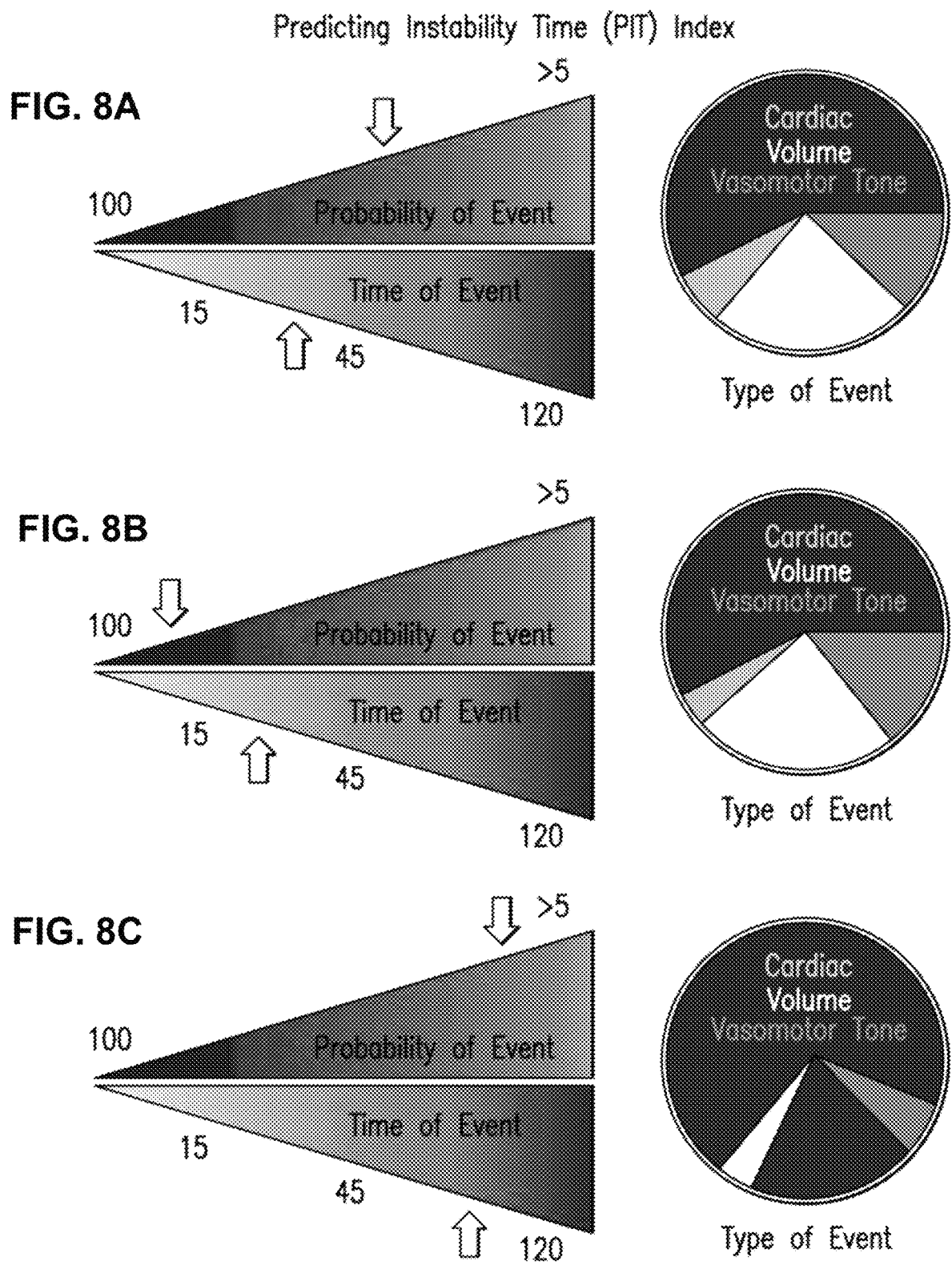

SYSTEM AND METHOD OF DETERMINING A SUSCEPTIBILITY TO CARDIORESPIRATORY INSUFFICIENCY

PRIORITY CLAIM

This application is a continuation of International Application No. PCT/US2012/045068, filed Jun. 29, 2012, which claims priority to U.S. Provisional Application No. 61/503,344, filed Jun. 30, 2011, priority to both of which is claimed, and the contents of both of which are hereby incorporated by reference in their entireties.

STATEMENT REGARDING FEDERALLY SPONSORED RESEARCH OR DEVELOPMENT

This invention was made with government support under grant numbers HL076157 and HL067181 awarded by the National Institutes of Health. The government has certain rights in the invention.

1. INTRODUCTION

The present application relates to a system and method for determining a patient's susceptibility of developing cardiorespiratory instability, determining an appropriate therapy, and defining when cardiorespiratory sufficiency has been achieved.

2. BACKGROUND OF THE INVENTION

Patients in a critical care setting are often vulnerable to a significant risk of developing cardiorespiratory instability. Although instability occurs in only a subset of hospitalized patients, it is associated with markedly increased mortality, which therefore makes the identification of those patients likely to become unstable crucial.

Several studies have demonstrated that a patient exhibiting abnormal cardiorespiratory vital signs at any point during hospitalization predicts increased mortality. Early instability typically manifests as subtle changes in multiple vital signs, while more pronounced single parameter abnormalities occur later.

Known methods are available to monitor and acquire non-invasive hemodynamic parameters to identify cardiorespiratory insufficiency in patients to a high degree, however no such mechanism exists to evaluate and/or predict the likelihood of a patient becoming cardiorespiratory unstable.

Several studies of in-hospital cardiac arrest demonstrate that significant physiological instability precedes arrest, but that it is often undetected or it is detected and not recognized as being serious. Early warning scores and modified early warning scores that calculate a single composite instability score from multiple vital signs have been helpful by providing caregivers with the ability to quantify concerns for instability and support for decisions to intervene or activate medical emergency teams. The compilation of warning scores however, can only define current—albeit more subtle—instability, but cannot predict who is likely to become unstable. As such, a need exists for improving clinical practice by recognizing patients at greater risk of developing cardiorespiratory insufficiency.

3. SUMMARY OF THE INVENTION

The disclosed subject matter provides a method for determining the susceptibility of a patient to develop cardiorespiratory instability relating to one or more physiological parameters. In a non-limiting embodiment, the method includes monitoring one or more physiological parameters associated with the patient, accessing a dynamics systems model directed to predicting a patient's likelihood of developing cardiorespiratory instability from patient data the includes measurements of the one or more physiological parameters, comparing measurements of at least one of the monitored one or more physiological parameters from the patient with the dynamics systems model, determining a susceptibility of the patient to develop cardiorespiratory instability, and indicating the susceptibility of the patient to develop cardiorespiratory instability. The method can further include generating a report indicating the susceptibility of the patient to develop cardiorespiratory instability and proposing an additional physiological parameter of the patient to be monitored and a corresponding effect such monitoring would have on the accuracy of the indicated susceptibility of the patient to develop cardiorespiratory instability.

In accordance with one embodiment of the disclosed subject matter, the susceptibility can comprise a susceptibility to develop cardiorespiratory instability between 0 and 30 minutes in the future. For example, the susceptibility can be indicated as a likelihood of developing at least one condition selected from hypovolemic, cardiogenic, or vasomotor tone dysfunction instability between 5 and 15 minutes in the future.

In a further embodiment, the dynamics systems model can include a defined physiological signature characteristic for hypovolemic, cardiogenic, and vasomotor tone dysfunction of the shock state.

In accordance with a further embodiment of the disclosed subject matter, the method can include determining responsiveness of the patient to an intervention including one or more of the following: fluid infusion, isotropic drug therapy, or vasopressor drug therapy. The determination of responsiveness of the patient to an intervention can be reported. The monitoring of the physiological parameters of the patient can be automatically adjusted in response to the determination of responsiveness.

In accordance with a further embodiment of the disclosed subject matter, the method can include determining whether the patient is responsive to a process-specific intervention. The determination of whether the patient is responsive to one or more process-specific intervention can be reported. The monitoring of the physiological parameters of the patient can be automatically adjusted in response to the determination of whether the patient is responsive to process-specific interventions.

In accordance with another embodiment of the disclosed subject matter, the method can include determining when resuscitation has effectively restored tissue perfusion and prevented the subsequent development of organ injury. The determination of when resuscitation has effectively restored tissue perfusion and prevented the subsequent development of organ injury can be reported. The monitoring of the physiological parameters of the patient can be automatically adjusted in response to the determination of when resuscitation has effectively restored tissue perfusion and prevented the subsequent development of organ injury.

In accordance with a further embodiment of the disclosed subject matter, monitoring the one or more physiological parameters can include monitoring one or more of the following: arterial blood pressure—i.e., systolic, diastolic—mean arterial pressure, systolic pressure variation, pulse pressure variation, stroke volume variation; right atrial pressure; right ventricular pressure; pulmonary artery pressure; mean pulmonary artery pressure; pulmonary artery wedge pressure; left atrial pressure; cardiac output; cardiac index; stroke volume; stroke index; stroke volume index; systemic vascular resistance; systemic vascular resistance index; pulmonary vascular resistance; pulmonary vascular resistance index; left ventricular stroke work; left ventricular stroke work index; right ventricular stroke work; right ventricular stroke work index; coronary artery perfusion pressure; right ventricular end-diastolic volume; right ventricular end-systolic volume; or, right ventricular ejection fraction. The method can further include monitoring one or more oxygenation parameters including: partial pressure of arterial oxygen; partial pressure of arterial CO2; bicarbonate; pH; arterial oxygen saturation; mixed venous saturation; arterial oxygen content; venous oxygen content; A-V oxygen content difference; oxygen delivery; oxygen delivery index; oxygen consumption; oxygen consumption index; oxygen extraction ration; or, oxygen extraction index, or monitoring one or more non-invasive vital signs including: heart rate; respiratory rate; blood pressure; peripheral arterial $O_2$ saturation ($SpO_2$); or, temperature.

The disclosed subject matter also provides systems and non-transitory computer readable media for determining the susceptibility of a patient to develop cardiorespiratory instability relating to one or more physiological parameters.

4. BRIEF DESCRIPTION OF THE DRAWINGS

FIG. 8A-C illustrates an example of visualization of a general output monitor. This display shows time to instability, accuracy of the ability to predict that an instability event will occur, and the underlying pathological cause of that instability.

5. DETAILED DESCRIPTION

The disclosed system and method utilize a multivariate model in cooperation with an integrated monitoring system (e.g., monitor) to routinely acquire physiological measurements of a patient and to identify with a high degree of precision those patients most likely to develop overt cardiorespiratory insufficiency—e.g., hemorrhagic, cardiogenic, and distributive shock—prior to the onset of overt hypotension and organ injury. The use of calibrated dynamical signals of diverse physiological variables provides for: an accurate prediction of cardiorespiratory insufficiency; a defined process-specific etiology(ies) for the pending instability; and, a measurable impact of increased monitoring with additional modalities or at alternative sampling frequencies; which may further result in an increased sensitivity and specificity than is currently available today. Moreover, a heightened universal treatment titration and a sufficiency achieved through (1) minimal lead time, (2) sampling frequency, and (3) independent variable inputs—referred to as hemodynamic monitoring parsimony—may also be achieved.

Additional benefits may include the ability to define the physiological signature characteristics of hypovolemic, cardiogenic, and vasomotor tone dysfunction as the primary etiologies of the shock state; as well as the ability to determine which additional biomarkers, increased lead time, and measuring frequencies will improve the accuracy of the prediction and the specificity of the etiology. Furthermore, it may be possible to determine whether a patient is responsive to process-specific interventions by demonstrating improvement, or if other interventions should be implemented. Still further, the determination of when resuscitation has effectively restored tissue perfusion and prevented the subsequent development of organ injury may also be attained.

Figure 1A:
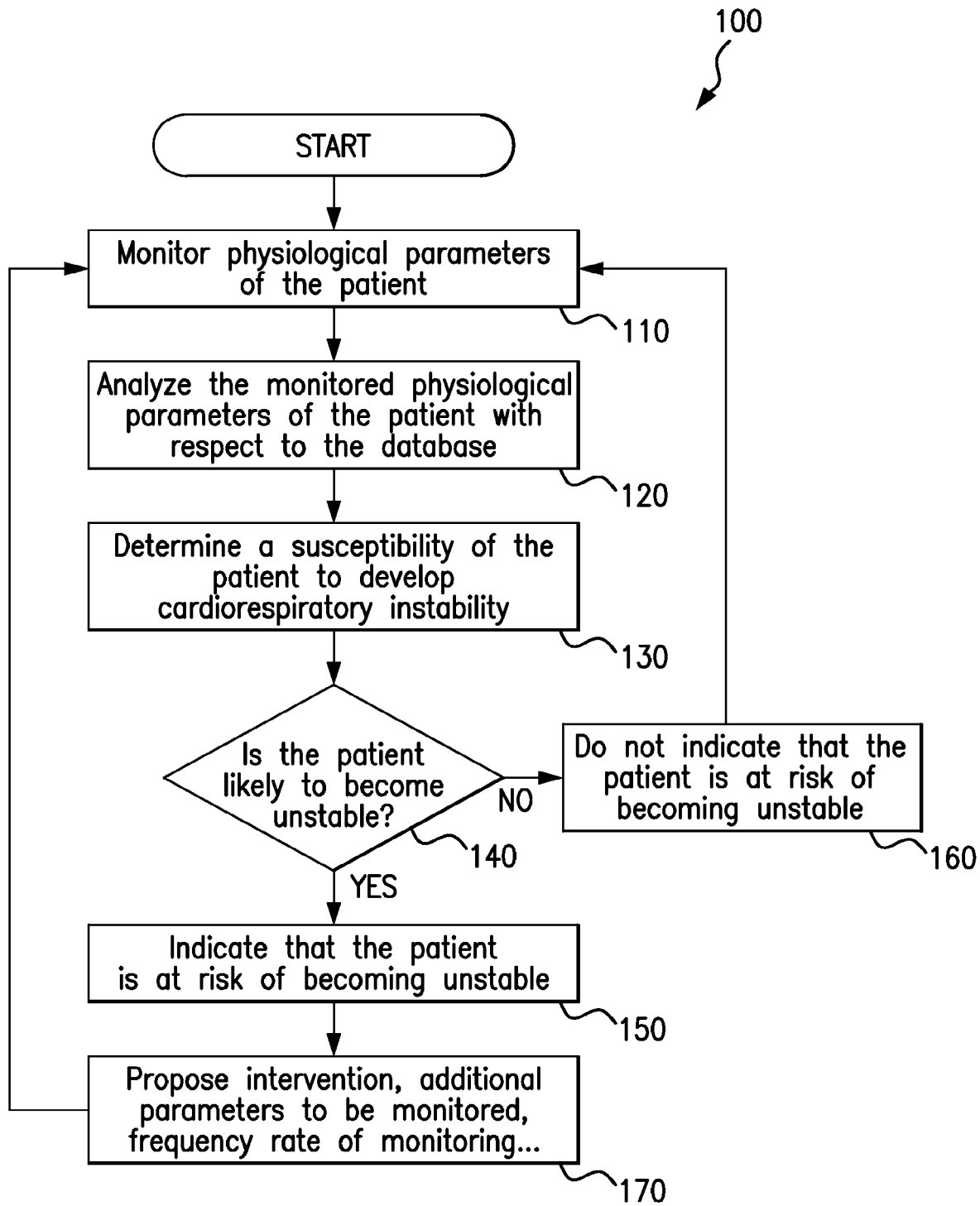
FIG. 1A illustrates an exemplary block diagram of a method for determining a patient's susceptibility of developing cardiorespiratory instability.

FIG. 1A illustrates an exemplary block diagram of a computer-implemented method 100 for assessing the susceptibility of a patient to develop cardiorespiratory instability relating to the dynamic interaction of one or more physiological parameters. The method may include monitoring (block 110) one or more physiological parameters—hemodynamic parameters—associated with the patient. The physiological parameters being monitored can be invasively (e.g., direct arterial blood pressure, pulmonary artery pressure, $StO_2$) or non-invasively (e.g., heart rate, respiratory rate, non-invasive blood pressure, $SpO_2$) acquired and include, at least, any combination of one or more of the following: arterial blood pressure (BP), i.e., systolic (SBP), diastolic (DBP)—mean arterial pressure (MAP), systolic pressure variation (SPV), pulse pressure variation (PPV), stroke volume variation (SVV); right atrial pressure (RAP); right ventricular pressure (RVP); pulmonary artery pressure (PAP); mean pulmonary artery pressure (MPAP); pulmonary artery wedge pressure (PAWP); left atrial pressure (LAP); cardiac output (CO); cardiac index (CI); stroke volume (SV); stroke volume index (SVI); systemic vascular resistance (SVR); systemic vascular resistance index (SVRI); pulmonary vascular resistance (PVR); pulmonary vascular resistance index (PVRI); left ventricular stroke work (LVSW); left ventricular stroke work index (LVSWI); right ventricular stroke work (RVSW); right ventricular stroke work index (RVSWI); coronary artery perfusion pressure (CPP); right ventricular end-diastolic volume (RVEDV); right ventricular end-systolic volume (RVESV); and, right ventricular ejection fraction (RVEF). Additionally, one or more oxygenation parameters can also be monitored; including, and not limited to: partial pressure of arterial oxygen ($PaO_2$); partial pressure of arterial $CO_2$ ($PaCO_2$); bicarbonate ($HCO_3$); pH; strong ion gap (SIG); arterial oxygen saturation ($SaO_2$); mixed venous saturation ($SvO_2$); arterial oxygen content ($CaO_2$); venous oxygen content ($CvO_2$); A-V oxygen content difference ($C(a-v)O_2$); oxygen delivery ($DO_2$); oxygen delivery index ($DO_2I$); oxygen consumption ($VO_2$); oxygen consumption index ($VO_2I$); oxygen extraction ration ($O_2ER$); oxygen extraction index ($O_2ERI$); and serum lactate. And, one or more non-invasive vital signs can likewise be monitored, including: heart rate (HR); respiratory rate (RR); blood pressure (BP); peripheral arterial $O_2$ saturation ($SpO_2$); and, temperature. Other aspects may also be considered, such as demographics, e.g., age, gender; and static clinical characteristics (unit admission and discharge dates and time, DRG codes, CPT codes, DRG weight, Charlson co-morbidity scores).

The method 100 may analyze (block 120) at least one of the monitored one or more physiological parameters associated with the patient with respect to one or more models associated with cardiorespiratory insufficiency. For simplicity, the collection of data, e.g., one or more models, stored in a memory device will be referred to herein as a database. This database may include a probabilistic model of normality in a plurality of dimensions previously learned from a representative set of patients at risk of developing cardiorespiratory insufficiency. The probabilistic model may be developed through the application of complex computational modeling concepts of dynamical systems; including and not limited to multivariable modeling, e.g., regression analysis, and machine learning (artificial neural networking) Variance from the probability dataset can be used to evaluate the likelihood that patient-derived physiological parameters are within an envelope of stability (block 130).

Depending upon whether a patient is deemed susceptible to becoming unstable (block 140), an indicator can be output reflecting the probability of instability (block 150, 160). If a patient is likely to become unstable, the system may propose intervention or emergency medical treatment, and/or request additional physiological parameters to monitor and analyze in an effort to increase the accuracy of the probability, and/or propose changes to the sampling frequency of parameters being monitored (block 170).

Figure 1B:
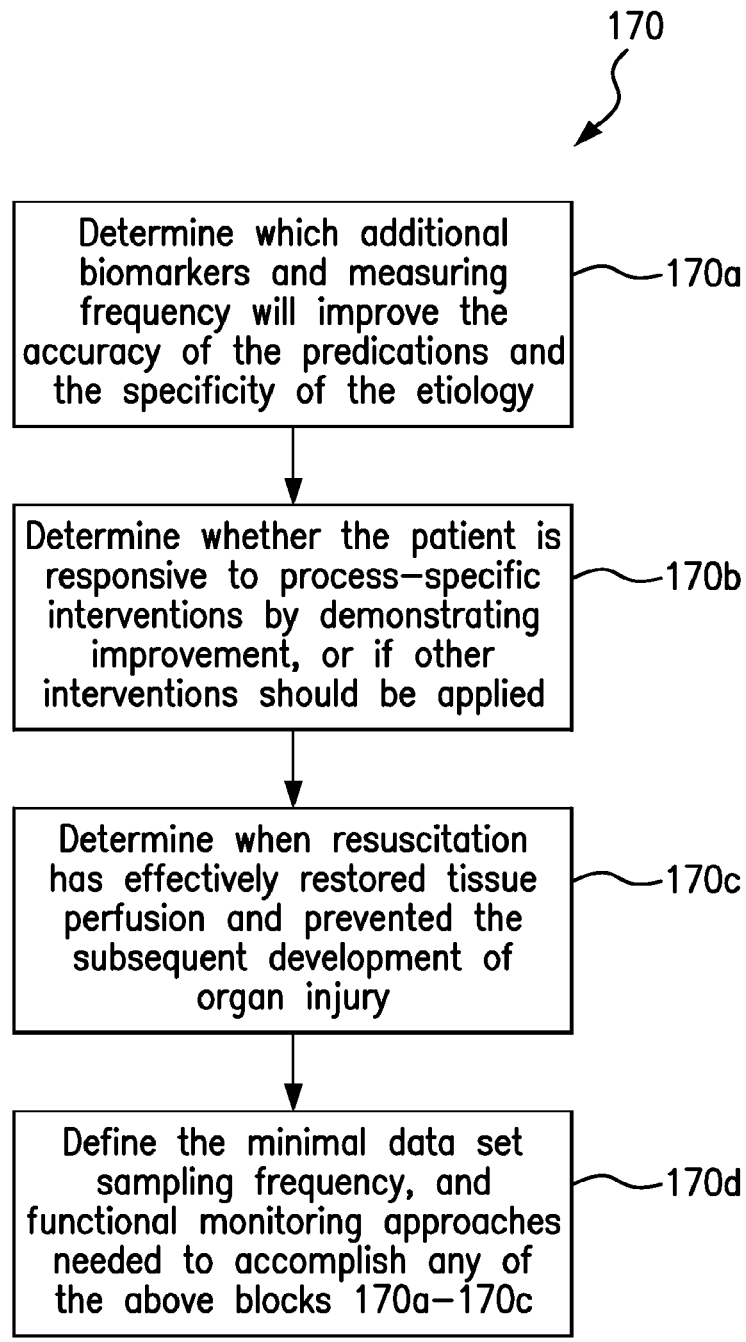
FIG. 1B illustrates an exemplary expansion of block 170 of the exemplary block diagram shown in FIG. 1.

Data suggests that dynamics of linkage between disparate physiological variables exist during disease, and these linkages—interconnections—may be used to identify patients and to define their primary illness. Furthermore, models can be utilized to best predict future instability with sensitivity, specificity, and data parsimony. In FIG. 1B, the output and proposals (block 170) can be expanded to include one or more further system determinations, such as: which additional biomarkers and measuring frequency will improve the accuracy of the predications and the specificity of the etiology (block 170a); whether the patient is responsive to process-specific interventions by demonstrating improvement, or if other interventions should be applied (block 170b); when resuscitation has effectively restored tissue perfusion and prevented the subsequent development of organ injury (block 170c); and, define the minimal data set, sampling frequency, lead time sampling duration, and functional monitoring approaches needed to accomplish the above (block 170d).

By way of example, the database can be generated by using mathematical concepts from dynamical systems theory to construct models for predicting instability (with probability) based on dynamical features/patterns. This approach may be appropriate due to the dynamical behavior of a patient being mathematically chaotic. As such, a patient has an "attractor," that is, a complex set comprising all the possible simultaneous values for his/her physiological parameters. In addition, there is a probability function associated with the attractor that expresses the fractional amount of time spent in different regions of the attractor. The attractor is stable, predictable, and determines the possible associations among the physiological variables. In contrast however, the instantaneous state—the values of the physiological parameters—is not predictable. Clinically relevant statements, such as, "the patient is 90% likely to have: 70<HR<90, 12<RR<20 in the next hour" are directly inferred from the probability function associated with the attractor. While health is usually thought of in terms of ranges of physiological variables (e.g., HR, RR), instability and the ability to predict it may depend more on dynamical signatures than the current state.

To understand the complexity related to regrouping of variables at different stages ranging from health to shock, hyper-graph theory can be employed. A hyper-graph consists of nodes—physiological variables—and hyper links to their groupings. Commercially—available software allows display of group—variables not readily discernable to the human eye but highly correlated by mathematical coupling. Non-limiting examples of such means of analysis include Artificial Neuronet (ANN), nearest neighbor and propensity scoring. The important concept here is not the actual mathematical process used to analyze the data stream but the output propensity and patterns that define specific pathological states. For example, analysis of a time series of data from animal models or human studies where known disease states are developing, such as hypovolemia (hemorrhage), display unique signatures of dynamical integrations that may become more defined as the pathological stress increases. Different physiological variables and their derived parameters presently allow accurate identification of existing disease states, but their changes over time presage the development of a worsening or improving physiological state. One of the main concepts that determine dynamical complexity is the dimensionality of the data and how many parameters may be useful to model the behavior of the patient and predict instabilities. Dynamics exist at all scales and each change in dynamical signatures is a candidate for being a predictor for progression into shock or recovery. Each of these dynamical signatures contains different information that may be useful for predicting instabilities. For example, dynamical signatures of hemodynamic parameters—including perhaps demographic and clinical characteristic data—of patients that became unstable and those that did not, can be utilized to improve predictions based on overt instability indicators. Thus, dynamical models can be built with a focus on determining the minimal data set—in terms of primary measured variables, sampling frequency, and lead time—required to: predict cardiorespiratory insufficiency, determine the etiology of cardiorespiratory insufficiency, and to predict that cardiorespiratory insufficiency has been resolved. We call this principal Hemodynamic Monitoring Parsimony. Such models may further determine and consider the value added to the minimal data set(s) in terms of increased specificity of increasing or changing measured variables, their sampling frequency, and lead time. Furthermore, various aspects of the dynamical signatures can be studied to discover key properties, such as: random noise at particular times, correlations among biomarkers, and the relation among the grouping of the biomarkers in a correlated set.

Figure 2:
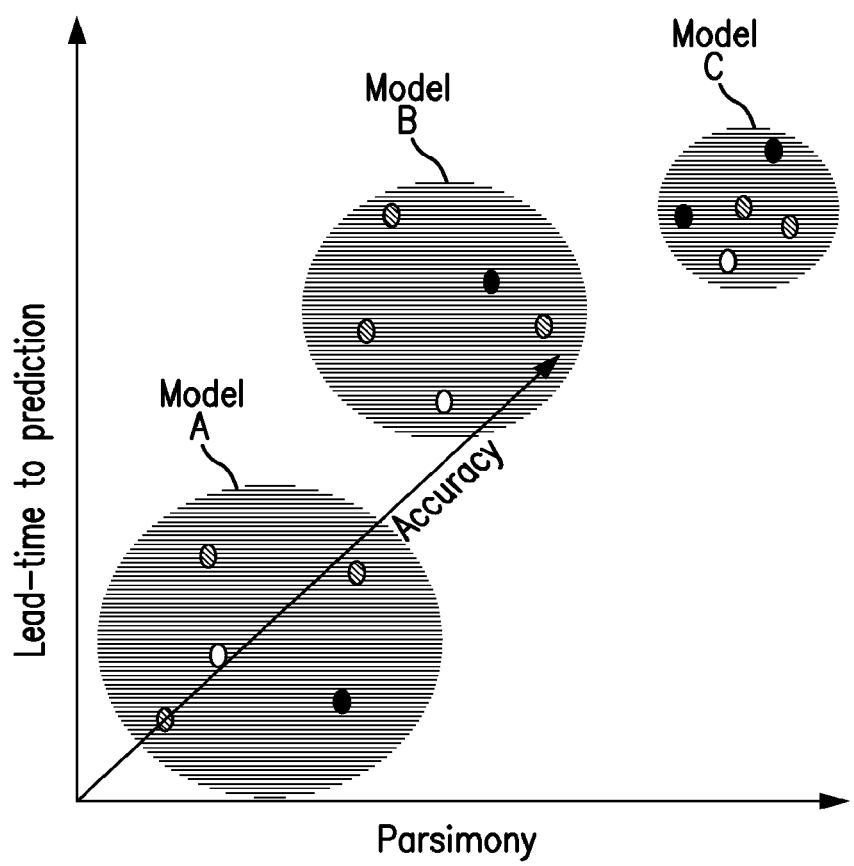
FIG. 2 illustrates the relationship among models relating to lead-time prediction, accuracy, and parsimony.

There are multiple ways to assess dimensionality and one of the most common is principal component analysis (PCA). Other approaches may involve all possible correlations between the parameters followed by clustering them into highly correlated groups. Models can be compared by predictive accuracy, parsimony, and lead-time to prediction; and trade-offs may exist there between depending upon the desired implementation. See FIG. 2. Any of these or other approaches can be implemented to compile the relevant information into an index value, which represents the predictability of future instability within a clinically relevant time.

Importantly, this complexity analysis of biomarker interactions is not limited to simple hemodynamic markers in the setting of acute illness but can also be applied as a system dynamical analysis to health care system delivery effectiveness, modeling patient-nursing staffing optimization, and cost-effectiveness analysis when the results relate to patient-centered outcomes.

Figure 3:
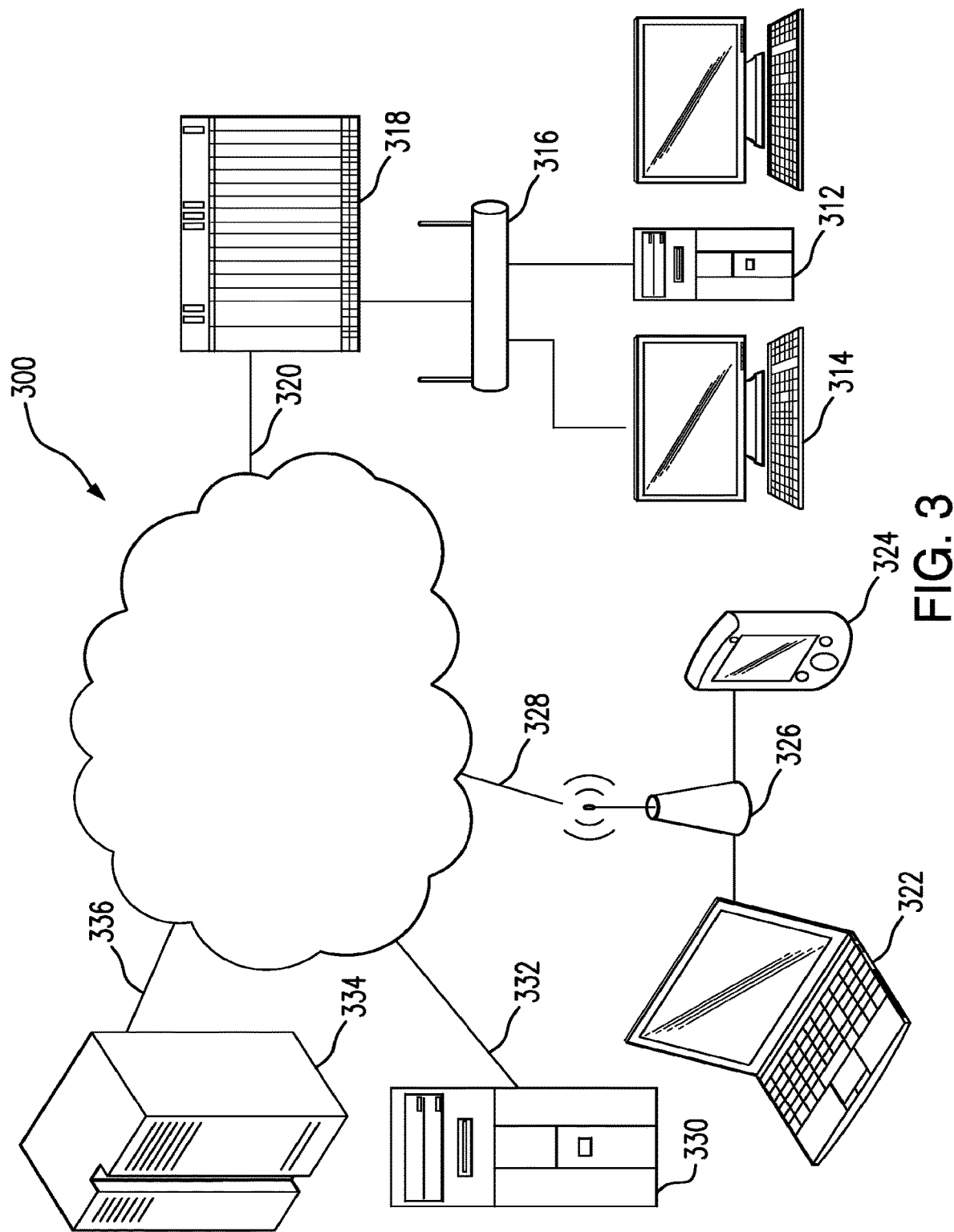
FIG. 3 illustrates an exemplary block diagram of a network and computer hardware that may be utilized in an exemplary system in accordance with the described embodiments.
Figure 4:
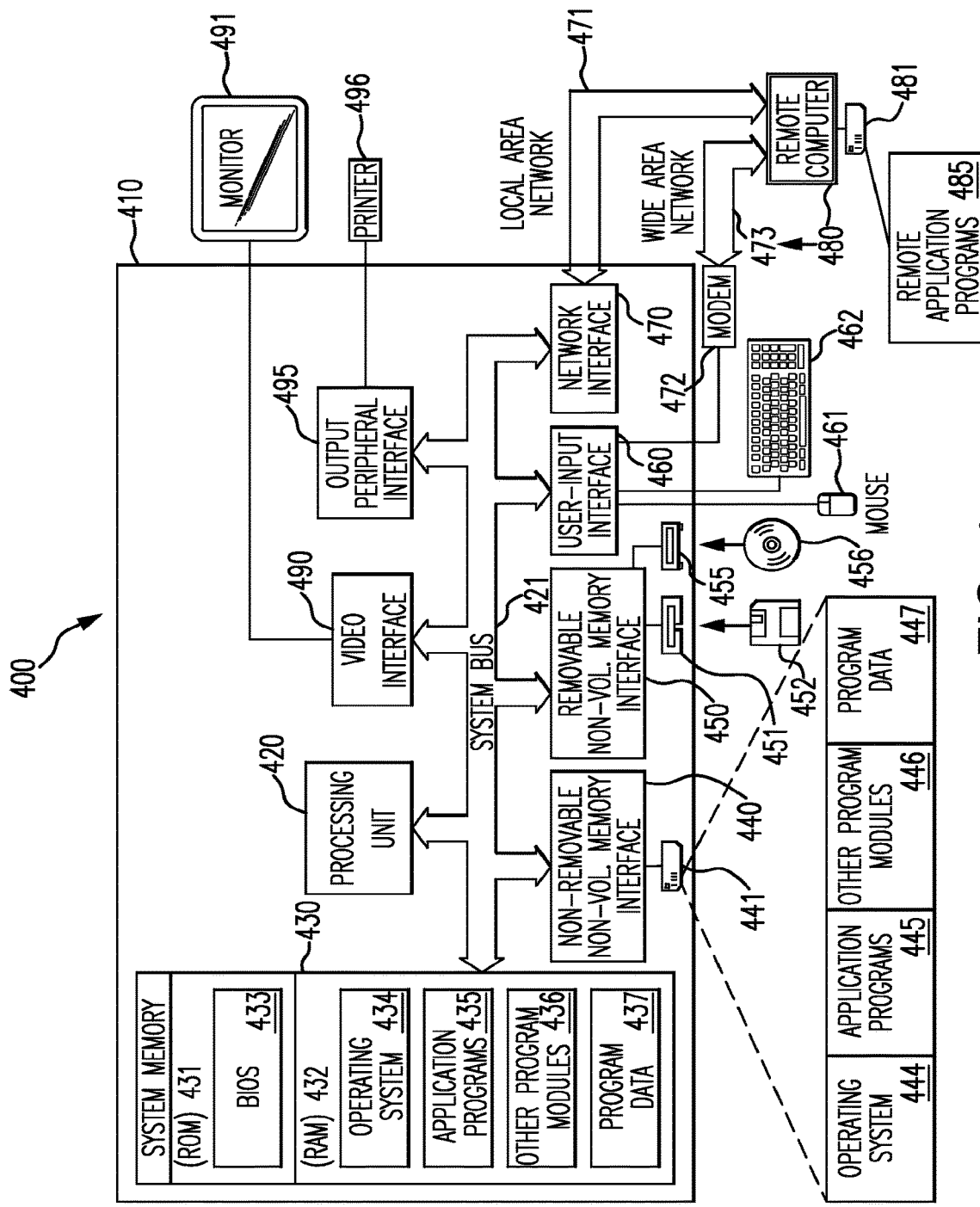
FIG. 4 illustrates an exemplary block diagram of a computer system on which an exemplary system may operate in accordance with the described embodiments.

The determination of a patient's susceptibility to cardiorespiratory insufficiency may be generated using an electronic system. FIGS. 3 and 4 provide an exemplary structural basis for the network and computational platforms related to such a system.

FIG. 3 illustrates an exemplary block diagram of a network 300 and computer hardware that may be utilized in an exemplary system for determining the probability of a patient to develop cardiorespiratory insufficiency in accordance with the described embodiments. The network 300 may be the Internet, a virtual private network (VPN), or any other network that allows one or more computers, communication devices, storage devices, etc., to be communicatively connected to each other. The network 300 may be connected to a personal computer 312, and a computer terminal 314 via an Ethernet 316 and a router 318, and a landline 320. The Ethernet 316 may be a subnet of a larger Internet Protocol network. Other networked resources, such as projectors or printers (not depicted), may also be supported via the Ethernet 316 or another data network. On the other hand, the network 300 may be wirelessly connected to a laptop computer 322 and a personal data assistant 324 via a wireless communication station 326 and a wireless link 328. Similarly, a server 330 may be connected to the network 300 using a communication link 332 and a mainframe 334 may be connected to the network 300 using another communication link 336. The network 300 may be useful for supporting peer-to-peer network traffic.

With respect to the determination of a patient's susceptibility to cardiorespiratory insufficiency described above, the one or more models associated with cardiorespiratory insufficiency and/or patient's monitored physiological parameters may be received over a network such as the network 300, for example. For example, a computer such as the personal computer 312, laptop computer 322, server 330 or mainframe 334 may receive the patient's monitored physiological parameters over the network 300. The patient's monitored physiological parameters may be received over the network 300 from an integrated monitoring system such as the personal computer 312, laptop computer 322, server 330 or mainframe 334, for example. The patient's monitored physiological parameters may also be received from a remotely-accessible, free-standing memory device on the network 300 (not shown). In some embodiments, the patient's monitored physiological parameters may be received by more than one computer. In other embodiments, the patient's monitored physiological parameters may be received from more than one computer and/or remotely-accessible memory device.

Some or all calculations performed in the determination of a patient's susceptibility to cardiorespiratory insufficiency described above (e.g., calculations for generating model data) may be performed by a computer such as the personal computer 312, laptop computer 322, server 330 or mainframe 334, for example. In some embodiments, some or all of the calculations may be performed by more than one computer.

Determining a patient's susceptibility to cardiorespiratory insufficiency, as described above in the embodiments, may also be performed by a computer such as the personal computer 312, laptop computer 322, server 330 or mainframe 334, for example. The indications may be made by setting the value of a data field, for example. In some embodiments, indicating a patient's susceptibility to developing cardiorespiratory insufficiency may include sending data over a network such as network 300 to another computer.

FIG. 4 illustrates an exemplary block diagram of a computer system 400 on which an exemplary method for determining a patient's susceptibility to cardiorespiratory insufficiency may operate in accordance with the described embodiments. The computer system 400 of FIG. 4 includes a computing device in the form of a computer 410. Components of the computer 410 may include, but are not limited to, a processing unit 420, a system memory 430, and a system bus 421 that couples various system components including the system memory to the processing unit 420. The processing unit 420 comprises one or more processors, with each processor implemented as one or more electronic circuits. The system bus 421 may be any of several types of bus structures including a memory bus or memory controller, a peripheral bus, and a local bus using any of a variety of bus architectures. By way of example, and not limitation, such architectures include the Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus (also known as Mezzanine bus).

Computer 410 typically includes a variety of non-transitory computer readable media. Non-transitory computer readable media can be any available media that can be accessed by computer 410 and includes both volatile and nonvolatile media, and both removable and non-removable media. By way of example, and not limitation, non-transitory computer readable media may comprise computer storage media. Computer storage media includes volatile and nonvolatile, removable and non-removable media implemented in any method or technology for storage of information such as computer readable instructions, data structures, program modules or other data. The computer readable instructions, when executed, can cause one or more processors to implement the steps of the disclosed subject matter. Various components of the disclosed system can be implemented as hardware, software, or any combination of hardware and software. For example, an index value calculator may be implemented as one or more processors and a computer readable media containing instructions that, when executed, cause the one or more processors to calculate an index value in accordance with the disclosed subject matter. Those having skill in the art will recognize that the hardware—in this case the one or more processors—implements any instructions provided in the software.

Computer storage media includes, but is not limited to, RAM, ROM, EEPROM, FLASH memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computer 410. The term "modulated data signal" means a signal that has one or more of its characteristics set or changed in such a manner as to encode information in the signal. Combinations of any of the above are also included within the scope of computer readable media.

Information can be received by or transmitted from a computer system over communication media. Communication media includes an information delivery media. By way of example, and not limitation, communication media includes wired media such as a wired network or direct-wired connection, and wireless media such as acoustic, radio frequency (RF), infrared and other wireless media. Computer readable instructions, data structures, program modules or other data can be received over communications media in the form of a modulated data signal such as a carrier wave or other transport mechanism. A person having ordinary skill in the art will understand that modulated data signals and the like are not themselves non-transitory computer readable media. Instead, information contained in the signal can be stored in a storage device (e.g., system memory or an optical storage device) to form the non-transitory computer readable media.

The system memory 430 includes computer storage media in the form of volatile and/or nonvolatile memory such as read only memory (ROM) 431 and random access memory (RAM) 432. A basic input/output system 433 (BIOS), containing the basic routines that help to transfer information between elements within computer 410, such as during start-up, is typically stored in ROM 431. RAM 432 typically contains data and/or program modules that are immediately accessible to and/or presently being operated on by processing unit 420. By way of example, and not limitation, FIG. 4 illustrates operating system 434, application programs 435, other program modules 436, and program data 437.

The computer 410 may also include other removable/non-removable, volatile/nonvolatile computer storage media. By way of example only, FIG. 4 illustrates a hard disk drive 441 that reads from or writes to non-removable, nonvolatile magnetic media, a magnetic disk drive 451 that reads from or writes to a removable, nonvolatile magnetic disk 452, and an optical disk drive 455 that reads from or writes to a removable, nonvolatile optical disk 456 such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 441 is typically connected to the system bus 421 through a non-removable memory interface such as interface 440, and magnetic disk drive 451 and optical disk drive 455 are typically connected to the system bus 421 by a removable memory interface, such as interface 450.

The drives and their associated computer storage media discussed above and illustrated in FIG. 4 provide storage of computer readable instructions, data structures, program modules and other data for the computer 410. In FIG. 4, for example, hard disk drive 441 is illustrated as storing operating system 444, application programs 445, other program modules 446, and program data 447. Note that these components can either be the same as or different from operating system 434, application programs 435, other program modules 436, and program data 437. Operating system 444, application programs 445, other program modules 446, and program data 447 are given different numbers here to illustrate that, at a minimum, they are different copies. A user may enter commands and information into the computer 410 through input devices such as a keyboard 462 and cursor control device 461, commonly referred to as a mouse, trackball or touch pad. A screen 491 or other type of display device is also connected to the system bus 421 via an interface, such as a graphics controller 490. In addition to the screen 491, computers may also include other peripheral output devices such as printer 496, which may be connected through an output peripheral interface 495.

The computer 410 may operate in a networked environment using logical connections to one or more remote computers, such as a remote computer 480. The remote computer 480 may be an integrated monitoring system operatively connected to a patient. The logical connections depicted in FIG. 4 include a local area network (LAN) 471 and a wide area network (WAN) 473, but may also include other networks. Such networking environments are commonplace in hospitals, offices, enterprise-wide computer networks, intranets, and the Internet.

When used in a LAN networking environment, the computer 410 is connected to the LAN 471 through a network interface or adapter 470. When used in a WAN networking environment, the computer 410 typically includes a modem 472 or other means for establishing communications over the WAN 473, such as the Internet. The modem 472, which may be internal or external, may be connected to the system bus 421 via the input interface 460, or other appropriate mechanism. In a networked environment, program modules depicted relative to the computer 410, or portions thereof, may be stored in the remote memory storage device 481. By way of example, and not limitation, FIG. 4 illustrates remote application programs 485 as residing on memory device 481.

The communications connections 470, 472 allow the device to communicate with other devices. The communications connections 470, 472 are an example of communication media. The communication media can carry computer reasonable instructions, data structures, program modules or other data in a modulated data signal such as a carrier wave or other transport mechanism. A "modulated data signal" may be a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media.

The embodiments for the methods of determining a patient's susceptibility of developing cardiorespiratory insufficiency described above may be implemented in part or in their entirety using one or more computer systems such as the computer system 400 illustrated in FIG. 4. The monitored physiological parameters and/or one or more models associated with cardiorespiratory insufficiency may be received by a computer such as the computer 410, for example. The monitored physiological parameters and/or one or more models associated with cardiorespiratory insufficiency may be received over a communication medium on a network such as local area network 471 or wide area network 473, via network interface 470 or user-input interface 460, for example. As another example, the monitored physiological parameters and/or one or more models associated with cardiorespiratory insufficiency may be received from a remote source such as the remote computer 480 where the data is initially stored on memory device such as the memory storage device 481. As another example, the monitored physiological parameters and/or one or more models associated with cardiorespiratory insufficiency may be received from a removable memory source such as the nonvolatile magnetic disk 452 or the nonvolatile optical disk 456. As another example, the monitored physiological parameters and/or one or more models associated with cardiorespiratory insufficiency may be received as a result of a human entering data through an input device such as the keyboard 462.

Some or all calculations performed in the determination of a patient's susceptibility to develop cardiorespiratory instability described above (e.g., calculations for generating a model(s) or determining the probability of a patient becoming unstable) may be performed by a computer such as the computer 410, and more specifically may be performed by one or more processors, such as the processing unit 420, for example. In some embodiments, some calculations may be performed by a first computer such as the computer 410 while other calculations may be performed by one or more other computers such as the remote computer 480. The calculations may be performed according to instructions that are part of a program such as the application programs 435, the application programs 445 and/or the remote application programs 485, for example. Each of the application programs 435, the applications programs 445, and the remote applications programs 485 can be implemented as non-transitory computer readable media, and when executed can cause one or more processors to perform the steps of the disclosed subject matter.

Determining a patient's susceptibility of developing cardiorespiratory instability as described above in the embodiments, may also be performed by a computer such as the computer 410. The indications may be made by setting the value of a data field stored in the ROM memory 431 and/or the RAM memory 432, for example. In some embodiments, indicating a patient's probability of becoming unstable may include sending data over a network such as the local area network 471 or the wide area network 473 to another computer, such as the remote computer 481. In other embodiments, indicating a patient's risk of becoming unstable may include sending data over a video interface such as the video interface 490 to display information relating to the prediction on an output device such as the screen 491 or the printer 496, for example.

In particular non-limiting embodiments, a method for determining the susceptibility of a patient to develop cardiorespiratory instability is provided, comprising:

(a) monitoring, over a time interval, one or more physiologic parameter selected from the group consisting of heart rate, blood oxygen saturation, and respiration rate and thereby generating a plurality of measurements of said parameter(s);

(b) calculating the test mean value and/or test standard deviation value over the interval for each parameter measured;

(c) accessing via a processor in a computer system having a memory, a dynamics system model that compares the mean values and/or standard deviation values of heart rate, blood oxygen saturation and/or respiration rates in patients that are either stable, unstable, or about to become unstable to generate model mean value(s) and/or model standard deviation value(s) for heart rate, blood oxygen saturation and/or respiration rate in unstable patients;

(d) comparing the test mean value(s) and/or test standard deviation value(s) calculated in (b) with the model mean value(s) and/or model standard deviation value(s) of patients who are about to become unstable in the dynamics system model;

(e) initiating additional or more frequent parameter monitoring where the comparison performed in (d) indicates that the patient is about to become unstable.

For example, but not by way of limitation, the parameter(s) may be measured over a plurality of intervals and a test mean value and/or test standard deviation value may be determined for each interval. In one non-limiting set of embodiments, the test values are compared between intervals. In certain subsets of such embodiments, the database includes a periodically updated set of clinical data including measurements of heart rate, blood oxygen saturation and/or respiration rate of patients such that the model mean value(s) and model standard deviation value(s) for patients that are stable, unstable, or about to become unstable are recalculated when or after the data is updated. For example, but not by way of limitation, the comparison of data or values may be performed by analysis of variance (ANOVA). By referring to a database that is updated, for example to include more patients and/or newer data, the ability to be able to, by comparison, predict that a patient is unstable would be expected to be refined over time and improve the predictive value. As a specific example, a database could be established in a hospital and updated to include new patient information, such that the likelihood that a new patient would become unstable could be predicted based on information gleaned from a well-matched control population (for example, comparison against locally generated values could offer better prediction than values produced based on data obtained in a different demographic).

As a specific non-limiting example, as reflected in working example 1, below, patient information in such a database may be analyzed to produce a model as follows. Heart rate (HR), respiratory rate (RR) and blood oxygen and SpO2 (oxygen saturation, for example as measured by a pulse oximeter) may be sampled at intervals, for example every minute or every second. Data streams may be divided in non-overlapping epochs of 5 minutes. For each epoch, means (EM) and standard deviations (ESD) may be computed for HR (EMHR, ESDHR), RR (EMRR, ESDRR), and SpO2 (EMSpO2, ESDSpO2). Instability may be defined as any one abnormality of HR<40 or >140, RR<8 or >36 and SpO2<85 occurring persistently for 4 minutes. Epochs may be classified as stable (S) if obtained from patients with no instability in their entire SDU stay, unstable (U) in the 60 minutes before meeting instability criteria, and pre-unstable (PU) otherwise. EM and ESD may be compared across S, U and PU and post hoc paired comparisons may be performed using Kruskal-Wallis ANOVA.

Although the final product(s) of the analysis described herein will be driven in large part by the specific patient groups and applications, for example Emergency Department rapid evaluations of impending cardiovascular collapse in recently admitted trauma patients, identification of impending cardiorespiratory insufficiency in previously stabilized step-down unit patients, stable but critically ill intensive care unit patients, out-patient dialysis patients and general outpatient monitoring over longer time intervals, a general output monitor can be visualized as shown in FIG. 8. This display shows three aspects of the approach: time to instability, accuracy of the ability to predict that an instability event will occur, and the underlying pathological cause of that instability.

In the example shown in FIG. 8, the time to a predicted instability event is 45 minutes and the probability of instability about 45%, whereas the proportion of pathological features contributing to this instability signal are primarily loss of effective circulating blood volume and vasomotor tone. These processes in a susceptible patient would strongly suggest to the bedside clinician or caregiver that the patient has impending septic shock or adrenal insufficiency, as these are the two processes that produce these conditions. The database created by the collection of many patient time series and more intensive monitoring and related measures (e.g. measure of blood chemistries, electrocardiogram, chest radiograph, etc.) would also suggest to the bedside clinician or caregiver that by measuring additional parameters at this point in time would increase the accuracy of the prediction making treatment more definitive (FIG. 8A).

In the example shown in FIG. 8B, measures of cardiac output and stroke volume variation (continuous and over time) when added to the non-invasive monitoring increases the accuracy of diagnosis of hypovolemia and loss of vasomotor tone. Based on these data within the context of the specific patient being monitored, the bedside clinician or caregiver can, for example, decide to treat the patient for presumed impeding septic shock by expanding antibiotic coverage, searching for an infectious source and rapid intravascular fluid resuscitation which markedly alters the predictive values (FIG. 8C) such that the time to instability has been increased from 45 minutes to >2 hrs and the probability of instability reduced to less than 15% and the size and amount of the physiological deficient markedly reduced. Thus, the monitoring clinician has real-time feedback that the process is being treated correctly and the negative cardiorespiratory event was avoided even though no actual cardiovascular collapse occurred to precipitate these treatments. Thus, septic shock is avoided and sepsis treated before the onset of tissue hypoperfusion.

Clearly, this form of monitoring and support can be done remotely and if validated as robust, in a closed loop fashion.

6. EXAMPLE 1: PHYSIOLOGIC VARIABLE ANALYSIS BETWEEN HEMODYNAMIC STABLE AND UNSTABLE PATIENTS

6.1 Materials and Methods

We retrospectively analyzed the continuous non-invasive integrated monitored data of 304 patients from a 24-bed step down unit (SDU) in a University-based medical center during 8 weeks from November 2006 to January 2007. HR, RR and $SpO_2$ were sampled every second. Data streams were divided in non-overlapping epochs of 5 minutes. For each epoch, means (EM) and standard deviations (ESD) were computed for HR (EMHR, ESDHR), RR (EMRR, ESDRR), and $SpO_2$ (EMSpO2, ESDSpO2). Instability was defined as any one abnormality of HR<40 or >140, RR<8 or >36 and $SpO_2$<85% occurring persistently for 4 minutes. Epochs were classified as stable (S) if obtained from patients with no instability in their entire SDU stay, unstable (U) in the 60 minutes before meeting instability criteria, and pre-unstable (PU) otherwise. EM and ESD were compared across S, U and PU and all post hoc paired comparisons performed using Kruskal-Wallis ANOVA.

6.2 Results and Discussion

Variability analysis of physiologic data in critically ill patients can suggest impending hemodynamic instability that may be targeted for early therapy prior to overt decompensation. We hypothesized that in a less critically ill population (in this study, patients in a SDU), stable patients and those destined to develop instability also have different distinctive physiologic profiles.

We found that 79 of 304 patients met criteria for instability. There were 194833, 948, and 40458 epochs available for analysis in S, U and PU respectively. The three groups differed significantly for all metrics (p=0.0001, Kruskal-Wallis) except ESDRR. EMHR, EMRR, and ESDSpO2 were higher while ESDHR and EMSpO2 were lower in U compared to PU, EMHR and EMSpO2 were higher while ESDHR, EMRR and ESDSpO2 were lower in PU compared to S (Table 1). These results were robust to modifying the threshold for defining PU to 120 minutes prior to instability, and confirm that stable patients have different physiological signatures than patients that will eventually develop instability. Further, the results illustrate that the profile of patients evolves in time prior to their developing instability.

TABLE 1

Mean (M) and Variability Index (VI) for HR, RR and $SpO_2$

| Variable | U | PU | S |
|---|---|---|---|
| $EM_{HR}$ | 86.84 (19.53)†† | 84.87 (18.06)* | 82.82 (15.79) |
| $ESD_{HR}$ | 2.43 (1.70)†† | 2.61 (1.82)* | 3.27 (2.56) |
| $EM_{RR}$ | 18.32 (6.37)† | 17.51 (4.64)* | 18.71 (4.11) |
| $ESD_{RR}$ | 2.45 (1.52) | 2.39 (1.42) | 2.37 (1.35) |
| $EM_{SpO2}$ | 92.08 (6.36)† | 96.53 (3.70)* | 96.16 (3.17) |
| $ESD_{SpO2}$ | 1.75 (2.04)† | 0.95 (1.20)* | 1.00 (1.14) |

†p < .0001;
††p < .007 (post hoc Kruskal-Wallis pairwise comparison, U vs. PU)
*p < 0.0001 (post hoc Kruskal-Wallis pairwise comparison, PU vs. S)

7. EXAMPLE 2: PHYSIOLOGIC VARIABLE ANALYSIS BETWEEN HEMODYNAMIC STABLE AND UNSTABLE PATIENTS

The data in Example 1 was further extended by 3 patients so that 307 patients were considered. In this data set, 78 patients were found to meet the criteria for instability.

Figures 5A, 5B:
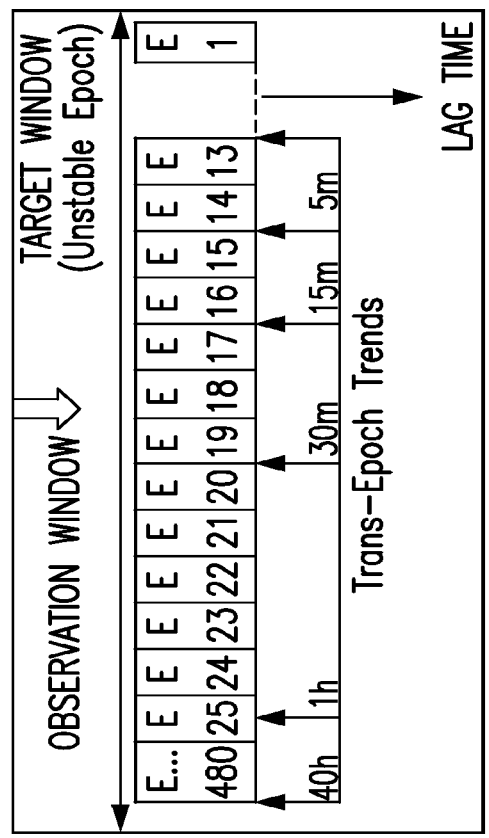
FIG. 5A shows features of derived 5 minute intervals regarding time, frequency and entropy
FIG. 5B is a schematic showing the observation window versus the target window.

FIG. 5A shows features of derived 5 minute intervals regarding time, frequency and entropy and FIG. 5B is a schematic showing the observation window versus the target window. Table 2, below shows univariate feature statistics across epoch types.

TABLE 2

| Variable | Unstable | Pre-Unstable | Stable |
|---|---|---|---|
| $EM_{HR}$ | 86.84 ± 19.53† | 84.87 ± 18.06* | 82.82 ± 15.79 |
| $ESD_{HR}$ | 2.43 ± 1.701† | 2.61 ± 1.82* | 3.27 ± 2.56 |
| $EM_{RR}$ | 18.32 ± 6.37† | 17.51 ± 4.64* | 18.71 ± 4.11 |
| $ESD_{RR}$ | 2.45 ± 1.52 | 2.39 ± 1.42 | 2.37 ± 1.35 |
| $EM_{SpO2}$ | 92.08 ± 6.36† | 96.53 ± 3.70* | 96.16 ± 3.17 |
| $ESD_{SpO2}$ | 1.75 ± 2.04† | 0.95 ± 1.20* | 1.00 ± 1.14 |
| $TP_{HR}$ (×10$^7$) | 6.39 ± 3.5† | 6.05 ± 2.87* | 5.74 ± 2.76 |
| $TP_{SpO2}$ (×10$^7$) | 6.74 ± 2.39† | 7.55 ± 2.20* | 7.49 ± 2.18 |
| $Ap_{HR}$ | 0.050 ± 0.036† | 0.057 ± 0.034* | 0.065 ± 0.036 |
| $Ap_{SpO2}$ | 0.024 ± 0.028† | 0.01 ± 0.019* | 0.016 ± 0.021 |
| $Se_{HR}$ | 1.30 ± 0.49† | 1.38 ± 0.50* | 1.50 ± 0.52 |
| $Se_{SpO2}$ | 0.87 ± 0.55† | 0.64 ± 0.45* | 0.66 ± 0.44 |
| $X_{HR-RR}$(×10$^9$) | 4.54 ± 2.26† | 4.20 ± 1.73* | 4.36 ± 1.67 |
| $XT_{HR-RR}$ | 3.57 ± 30.6† | 0.237 ± 7.56 | 0.10 ± 5.39 |

HR = Heart rate.
RR = Respiratory rate.
SpO2 = pulse oximeter.
EM = Epoch mean.
ESD = Epoch standard deviation.
TP = Total power.
Ap = Approximate entropy.
Se = Sample entropy.
X = Maximal cross-correlation.
XT = Cross-correlation memory.
†p < 0.01 (post-hoc Kruskal-Wallis pairwise comparison) Unstable vs. Pre-Unstable
*p < 0.01 (post-hoc Kruskal-Wallis pairwise comparison) Pre-Unstable vs. Stable.

Figure 6:
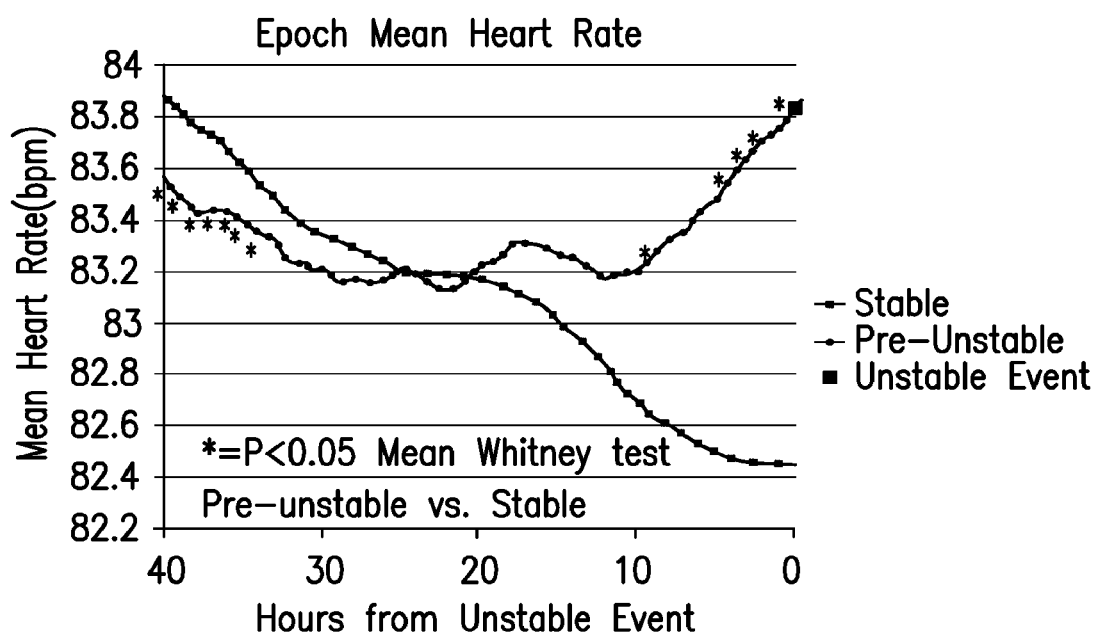
FIG. 6 shows historic epoch trends, where pre-unstable and stable epoch mean heart rate profiles differ over time.
Figure 7:
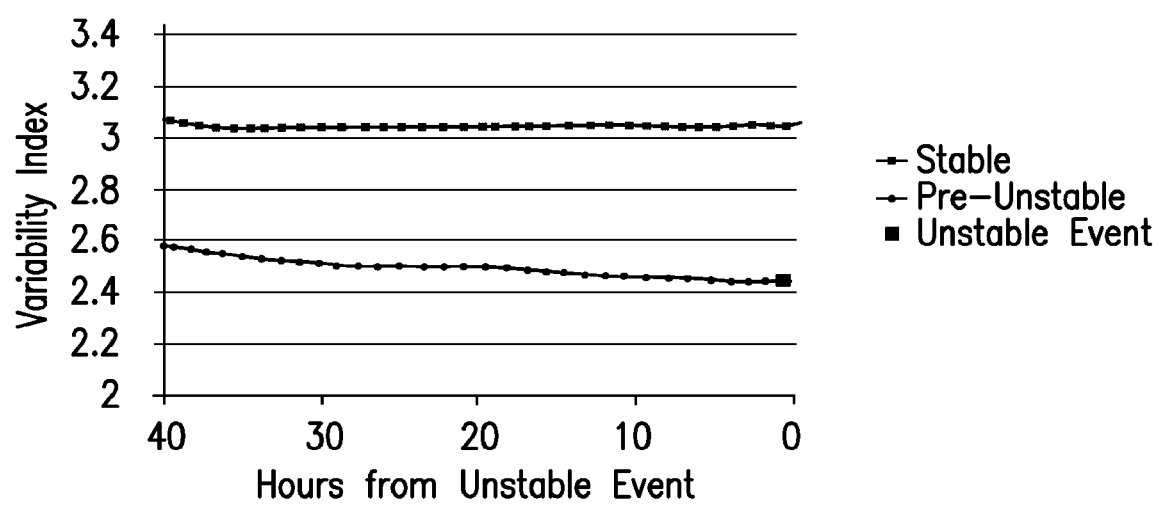
FIG. 7 shows that pre-unstable patient epochs exhibit less heart rate variability than stable patient epochs.

As shown in FIG. 6, in historic epoch trends, pre-unstable and stable epoch mean heart rate profiles differ over time. Pre-unstable patient epochs exhibit less heart rate variability than stable patient epochs (FIG. 7). Table 3 shows that trans-epoch trends correlate with pre-unstable, unstable and stable epochs.

TABLE 3

| 5 mins | 15 mins | 30 mins | 60 mins | 120 mins |
|---|---|---|---|---|
|  | $EM_{HR}$ | $EM_{HR}$ | $EM_{HR}$ |  |
| $EM_{SpO2}$ | $EM_{SpO2}$ | $EM_{SpO2}$ | $EM_{SpO2}$ | $EM_{SpO2}$ |
|  | $ESD_{SpO2}$ | $ESD_{SpO2}$ | $ESD_{SpO2}$ | $ESD_{SpO2}$ |
| $TP_{HR}$ | $HI_{SpO2}$ | $TP_{SpO2}$ | $TP_{SpO2}$ | $TP_{SpO2}$ |
|  | $Ap_{SpO2}$ | $Ap_{SpO2}$ | $Ap_{SpO2}$ | $Ap_{SpO2}$ |
|  | $Se_{SpO2}$ | $Se_{SpO2}$ | $Se_{SpO2}$ | $Se_{SpO2}$ |
| $XT_{HR-RR}$ |  | $XT_{HR-RR}$ | $XT_{HR-RR}$ | $XT_{HR-RR}$ |
|  |  |  |  | $X_{HR-SpO2}$ |
|  |  |  |  | $X_{HR-SpO2}$ |

Various publications, patent applications, and patents are set forth herein, the contents of which are hereby incorporated by reference in their entireties.

I claim:

1. A method for determining the susceptibility of a patient to develop cardiorespiratory instability relating to one or more physiological parameters, the method comprising:
    monitoring, via one or more sensors operatively coupled to the patient, one or more physiological parameters associated with the patient;
    accessing, via one or more processors, a dynamics systems model directed to predicting the patient's likelihood of developing cardiorespiratory instability, using measurements of the one or more physiological parameters from the one or more sensors, wherein the dynamics system model includes a periodically updated set of clinical data including measurements of the one or more physiological parameters from a plurality of patients at risk of developing cardiorespiratory insufficiency such that the dynamics model is recalculated when or after the clinical data from the plurality of patients is updated;
    comparing, via the one or more processors, measurements of at least one of the monitored one or more physiological parameters from the patient with the recalculated dynamics systems model;
    determining, via the one or more processors, a similarity between the physiological parameters from the patient and the recalculated dynamics systems model for a susceptibility of the patient to develop cardiorespiratory instability; and,
    indicating, via a display coupled to the one or more processors, how the physiological parameters from the patient fit the recalculated dynamics systems model for the susceptibility of the patient to develop cardiorespiratory instability.

2. The method of claim 1, further comprising generating a report indicating how the physiological parameters from the patient fit the recalculated dynamics systems model for the susceptibility of the patient to develop cardiorespiratory instability.

3. The method of claim 1, wherein the physiological parameters from the patient fit the recalculated dynamics systems model for a susceptibility to develop cardiorespiratory instability between 0 and 30 minutes in the future.

4. The method of claim 3, wherein the physiological parameters from the patient fit the recalculated dynamics systems model for a likelihood of developing at least one condition selected from hypovolemic, cardiogenic, or vasomotor tone dysfunction between 5 and 15 minutes in the future.

5. The method of claim 1 further including proposing, via the one or more processors, an additional physiological parameter of the patient to be monitored and a corresponding effect such monitoring would have on the accuracy of how the physiological parameters from the patient fit the recalculated dynamics systems model for the patient to develop cardiorespiratory instability.

6. The method of claim 1, wherein the dynamics systems model includes a defined physiological signature characteristic for hypovolemic, cardiogenic, and vasomotor tone dysfunction of the shock state.

7. The method of claim 1, further including determining, via the one or more processors, responsiveness of the patient to an intervention including one or more of the following: fluid infusion, inotropic drug therapy, or vasopressor drug therapy.

8. The method of claim 7 further including reporting the determination of responsiveness of the patient to an intervention.

9. The method of claim 7 further including automatically adjusting the monitoring of the physiological parameters of the patient in response to the determination of responsiveness.

10. The method of claim 7 further including automatically adjusting the monitoring of the physiological parameters of the patient in response to the determination of whether the patient is responsive to process-specific interventions.

11. The method of claim 1, further including determining, via the one or more processors, whether the patient is responsive to process-specific interventions by demonstrating improvement, or if other interventions should be applied.

12. The method of claim 11 further including reporting whether the patient is responsive to process-specific interventions.

13. The method of claim 1, further including determining, via the one or more processors, when resuscitation has effectively restored tissue perfusion and prevented the subsequent development of organ injury.

14. The method of claim 13 further including reporting the determination of when resuscitation has effectively restored tissue perfusion and prevented the subsequent development of organ injury.

15. The method of claim 13 further including automatically adjusting the monitoring of the physiological parameters of the patient in response to the determination of when resuscitation has effectively restored tissue perfusion and prevented the subsequent development of organ injury.

16. The method of claim 1, wherein monitoring the one or more physiological parameters includes monitoring one or more of the following: arterial blood pressure—i.e., systolic, diastolic—mean arterial pressure, systolic pressure variation, pulse pressure variation, stroke volume variation; heart rate and entropy; right atrial pressure; right ventricular pressure; pulmonary artery pressure; mean pulmonary artery pressure; pulmonary artery wedge pressure; left atrial pressure; cardiac output; cardiac index; stroke volume; stroke index; stroke volume index; systemic vascular resistance; systemic vascular resistance index; pulmonary vascular resistance; pulmonary vascular resistance index; left ventricular stroke work; left ventricular stroke work index; right ventricular stroke work; right ventricular stroke work index; coronary artery perfusion pressure; right ventricular end-diastolic volume; right ventricular end-systolic volume; or, right ventricular ejection fraction.

17. The method of claim 16, wherein monitoring the one or more physiological parameters includes monitoring one or more oxygenation parameters including: partial pressure of arterial oxygen; partial pressure of arterial CO2; bicarbonate; pH; arterial oxygen saturation; mixed venous saturation; arterial oxygen content; venous oxygen content; A-V oxygen content difference; oxygen delivery; oxygen delivery index; oxygen consumption; oxygen consumption index; oxygen extraction ration; or, oxygen extraction index.

18. The method of claim 17, wherein monitoring the one or more physiological parameters further includes monitoring one or more non-invasive vital signs including: heart rate; respiratory rate; blood pressure; peripheral arterial O2 saturation (SpO2); or, temperature.

19. The method of claim 1, wherein the dynamics systems model comprises a plurality of independent time series variables to define cardiorespiratory instability.

20. The method of claim 1, wherein the clinical data is periodically updated to include clinical data from new patients.

21. The method of claim 1, wherein the dynamics systems model includes demographic data of the plurality of patients.

22. The method of claim 21, wherein the dynamics systems model is periodically updated to include information from a portion of the plurality of patients selected based on the demographic data.

23. A non-transitory computer-readable storage medium comprising computer-readable instructions stored thereon that when executed by a processor, causes the processor to perform a method for determining the susceptibility of a patient to develop cardiorespiratory instability relating to one or more physiological parameters, the method comprising:
monitoring, via one or more sensors operatively coupled to the patient, one or more physiological parameters associated with the patient; analyzing at least one of the monitored one or more physiological parameters;
accessing a dynamics systems model directed to predicting the patient's likelihood of developing cardiorespiratory instability, wherein the dynamics system model includes a periodically updated set of clinical data including measurements of the one or more physiological parameters from a plurality of patients at risk of developing cardiorespiratory insufficiency such that the dynamics model is recalculated when or after the clinical data from the plurality of patients is updated;
comparing at least one of the analyzed physiological parameters with the recalculated dynamics systems model;
determining a similarity between the physiological parameters from the patient and the recalculated dynamics systems model for a susceptibility of the patient to develop cardiorespiratory instability; and,
indicating, via a display, how the physiological parameters from the patient fit the recalculated dynamics systems model for the susceptibility of the patient to develop cardiorespiratory instability.

24. The non-transitory computer-readable storage medium of claim 23, further including proposing an additional physiological parameter of the patient to be monitored and a corresponding effect such monitoring would have on the accuracy of how the physiological parameters from the patient fit the dynamics systems model for the patient to develop cardiorespiratory instability.

25. The non-transitory computer-readable storage medium of claim 23, wherein the dynamics systems model includes a defined physiological signature characteristic for hypovolemic, cardiogenic, and vasomotor tone dysfunction of the shock state.

26. The non-transitory computer-readable storage medium of claim 23, wherein the dynamics systems model includes a probabilistic model of normality in a plurality of dimensions previously learned from a representative set of a plurality of patients at risk of developing cardiorespiratory insufficiency.

27. The non-transitory computer-readable storage medium of claim 23, further including determining responsiveness of the patient to an intervention.

28. A system for determining the susceptibility of a patient to develop cardiorespiratory instability relating to one or more physiologic parameters, the system comprising:
an integrated monitoring system including a processor, a display device, and one or more sensors, the one or more sensors are operatively connected to the patient to monitor one or more physiological parameters of the patient a memory coupled to the integrated monitoring system;
a memory device storing one or more dynamics systems models directed to predicting the patient's likelihood of developing cardiorespiratory instability;
one or more processors configured to produce an index output that indicates a susceptibility of the patient to develop cardiorespiratory instability based at least in part on at least one of the monitored one or more physiological parameters of the patient and at least one of the one or more dynamics systems models; and
a display device configured to display the index output.

29. The system of claim 28 wherein the index output includes a proposal to monitor an additional physiological parameter of the patient and a corresponding effect such monitoring would have on the accuracy of the indicated susceptibility of the patient to develop cardiorespiratory instability.

30. The system of claim 28, wherein the one or more dynamics systems models includes a defined physiological signature characteristic for hypovolemic, cardiogenic, and vasomotor tone dysfunction of the shock state.

31. The system of claim 28, wherein the one or more dynamics systems models includes a probabilistic model of normality in a plurality of dimensions previously learned from a representative set of a plurality of patients at risk of developing cardiorespiratory insufficiency.

32. The system of claim 28, wherein the one or more dynamics systems models is directed to determining a minimal data set—in terms of measure variables and their respective sampling frequencies and lead times—required to predict cardiorespiratory insufficiency.

33. The system of claim 28, wherein the one or more dynamics systems models directed to determining a minimal data set required to predict cardiorespiratory insufficiency is constructed with a focus on increased specificity of increasing or changing measured variables, their sampling frequency, and lead time.

34. The system of claim 28, wherein the one or more dynamics systems models is directed to determining a minimal data set—in terms of measure variables and their respective sampling frequencies and lead times—required to determine an etiology of cardiorespiratory insufficiency.

35. The system of claim 34, wherein the one or more dynamics systems models directed to determining a minimal data set required to determine an etiology of cardiorespiratory insufficiency is constructed with a focus on increased specificity of increasing or changing measured variables, their sampling frequency, and lead time.

36. The system of claim 28, wherein the one or more dynamics systems models is directed to determining a minimal data set—in terms of measure variables and their respective sampling frequencies and lead times—required to predict that cardiorespiratory insufficiency has been resolved.

37. The system of claim 36, wherein the one or more dynamics systems models directed to determining a minimal data set required to predict that cardiorespiratory insufficiency has been resolved is constructed with a focus on increased specificity of increasing or changing measured variables, their sampling frequency, and lead time.

38. A method for determining the susceptibility of a patient to develop cardiorespiratory instability comprising:
    (a) monitoring, over a time interval, one or more physiologic parameter selected from the group consisting of heart rate, blood oxygen saturation, and respiration rate and thereby generating a plurality of measurements of said parameter(s);
    (b) calculating the test mean value and/or test standard deviation value over the interval for each parameter measured;
    (c) accessing via one or more processors in a computer system having a memory, a dynamics system model that compares the mean values and/or standard deviation values of heart rate, blood oxygen saturation and/or respiration rates in patients that are either stable, unstable, or about to become unstable to generate model mean value(s) and/or model standard deviation value(s) for heart rate, blood oxygen saturation and/or respiration rate in unstable patients;
    (d) comparing the test mean value(s) and/or test standard deviation value(s) calculated in (b) with the model mean value(s) and/or model standard deviation value(s) of patients who are about to become unstable in the dynamics system model;
    (e) initiating additional or more frequent parameter monitoring where the comparison performed in (d) indicates that the patient is about to become unstable.

39. The method of claim 38 wherein a memory device stores a periodically updated set of clinical data including measurements of heart rate, blood oxygen saturation and/or respiration rate of patients such that the model mean value(s) and model standard deviation value(s) for patients that are stable, unstable, or about to become unstable are recalculated when or after the data is updated.

40. The method of claim 38 where the comparison of data or values is performed by analysis of variance (ANOVA).

41. The method of claim 38, where the parameter(s) is/are measured over a plurality of intervals and a test mean value and/or test standard deviation value is determined for each interval.

42. The method of claim 41 where the test values are compared between intervals.

* * * * *